United States Patent [19]

Regnier et al.

[11] Patent Number: 5,734,077

[45] Date of Patent: Mar. 31, 1998

[54] SUBSTITUTED 2,2-DIMETHYL-OMEGA-PHENOXYALKANOIC ACIDS AND ESTERS

[75] Inventors: Gilbert Regnier, Chatenay Malabry; Claude Guillonneau, Clamart; Jean-Paul Vilaine, Chatenay Malabry; Florence Mahlberg, Saint Cloud; Christine Breugnot, Paris, all of France

[73] Assignee: Adir ET Compagnie, Courbevoie, France

[21] Appl. No.: 713,665

[22] Filed: Sep. 13, 1996

[30] Foreign Application Priority Data

Sep. 14, 1995 [FR] France ................... 95 10731

[51] Int. Cl.$^6$ .................... C07C 59/48
[52] U.S. Cl. ............ 562/471; 562/431; 560/17; 560/9; 560/61; 560/55; 514/532; 514/543; 514/571
[58] Field of Search ............ 562/471, 431; 560/17, 61, 55; 514/532, 543, 571

[56] References Cited

FOREIGN PATENT DOCUMENTS 51-1008228  1/1976  Japan.

*Primary Examiner*—Paul J. Killos
*Attorney, Agent, or Firm*—The Firm of Gordon W. Hueschen

[57] ABSTRACT

New substituted 2,2-dimethyl-ω-phenoxyalkanoic acids and esters of formula:

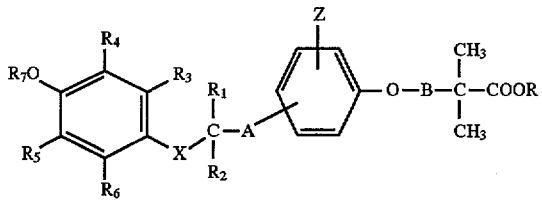

wherein:

X, A, B, R, $R_1$, $R_2$, $R_3$, $R_4$, $R_5$, $R_6$, $R_7$ and Z are as defined in the specification, The corresponding enantiomers and diastereoisomers, and the physiologically tolerable salts thereof with appropriate bases.

The products of the invention may be used therapeutically.

9 Claims, No Drawings

SUBSTITUTED 2,2-DIMETHYL-OMEGA-PHENOXYALKANOIC ACIDS AND ESTERS

The present invention relates to new substituted 2,2-dimethyl-ω-phenoxyalkanoic acids and esters.

It relates more especially to compounds of formula I:

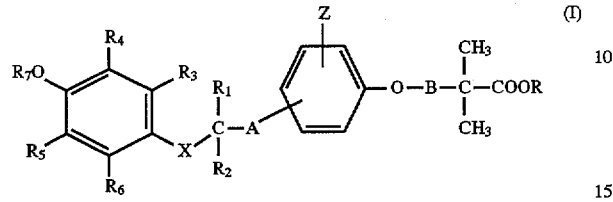

wherein:

X represents an oxygen atom, a sulfur atom or a single bond;

A represents a single bond, or a hydrocarbon radical having from 1 to 9 carbon atoms in straight or branched chain and optionally containing a double bond or an oxygen atom;

B represents a hydrocarbon radical having from 1 to 9 carbon atoms in straight or branched chain;

R represents a hydrogen atom, or an alkyl radical having from 1 to 6 carbon atoms in straight or branched chain that is optionally substituted by one or two hydroxy radicals;

$R_1$ and $R_3$:

each simultaneously represents a hydrogen atom, or together form a $(CH_2)_n$ bridge wherein n has a value of 1 or 2 except in the case where X represents a single bond, or $R_1$ represents a methyl radical, or a single bond forming a double bond with the group A when that group is a hydrocarbon radical and, in each of those cases $R_3$ simultaneously represents a hydrogen atom;

$R_2$ and $R_6$, which are identical or different, each represents a hydrogen atom or a methyl radical;

$R_4$ and $R_5$, which are identical or different, each represents an alkyl radical having from 1 to 6 carbon atoms in straight or branched chain;

$R_7$ represents a hydrogen atom or a labile protecting group such as, for example, a $CH_3CO-$, $C_2H_5OCH_2-$ or benzyl radical; and Z represents a hydrogen or halogen atom or an alkyl or alkoxy radical each having from 1 to 5 carbon atoms in straight or branched chain.

Some compounds of formula I comprise one or more chiral atoms and may therefore exist in the form of enantiomers or diastereoisomers, which also form part of the present invention.

On the other hand, the compounds of formula I that contain a double bond may exist in the E or Z form, each of which forms a part of the present invention.

Also, compounds of formula I wherein R represents a hydrogen atom may be converted into addition salts with pharmaceutically acceptable bases, those salts, as such, being included in the present invention.

The closest prior art to the present invention is illustrated by U.S. Pat. No. 4,752,616 which relates, inter alia, to thioalkylphenylalkanoic acids and esters of formula:

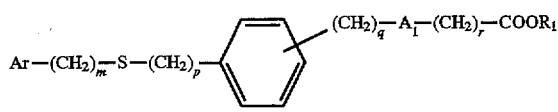

wherein:

Ar represents, inter alia, an optionally substituted phenyl radical;

Al is a group of the formula:

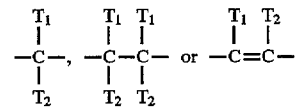

($T_1$ and $T_2$ being hydrogen or lower alkyl);

m is zero, 1, 2 or 3;

p is an integer of from 1 to 5;

q is zero, 1, 2 or 3:

r is zero, 1 or 2; and $R_1$ is hydrogen, lower alkyl or an alkali metal.

The said compounds are anti-thrombotic, anti-asthmatic and vasodilatory agents.

The compounds of the present invention differ from the known prior art compounds defined above both in their chemical structure and in their pharmacological and therapeutic activity which derives from their antioxidant effect demonstrated in respect of human LDLs (low density lipoproteins) and from their hypolipaemic affect.

The present invention relates also to a process for the preparation of compounds of formula I which is characterised in that:

a) a compound of formula IIa:

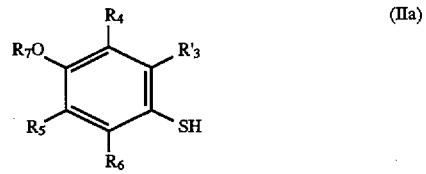

wherein:

$R_4$, $R_5$, $R_6$ and $R_7$ are as defined above and $R'_3$ represents a hydrogen atom, is reacted with a compound of formula IIIa:

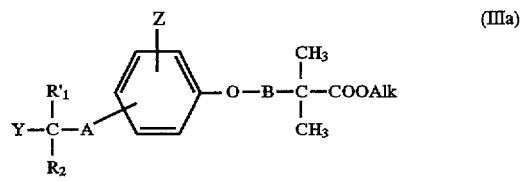

wherein:

A, B, $R_2$ and Z are as defined above, $R'_1$ represents a hydrogen atom or a methyl radical;

Alk represents an alkyl radical having from 1 to 6 carbon atoms in straight or branched chain, and Y represents a chlorine or bromine atom;

to obtain a compound of formula Ia₁:

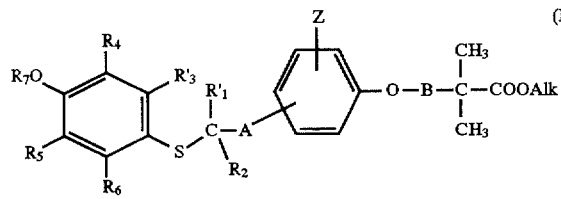  (Ia₁)

wherein R'₁, R₂, R'₃, R₄, R₅, R₆, R₇, A, Z, B and Alk are as defined above, which compound Ia₁ is, depending on the nature of R₇, converted by sequential methods of saponification, hydrolysis or hydrogenolysis into a compound of formula Ia₂:

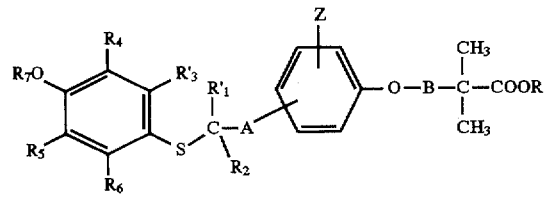  (Ia₂)

wherein R'₁, R₂, R'₃, R₄, R₅, R₆, R₇, A, Z, B and R are as defined above;

b) or a compound of formula IIb:

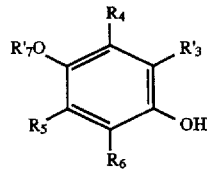  (IIb)

wherein:

R'₃, R₄, R₅ and R₆ are as defined above, and

R'₇ represents a labile protecting group, such as CH₃—CO—, C₂H₅—O—CH₂ or benzyl;

is reacted with a compound of formula IIIb:

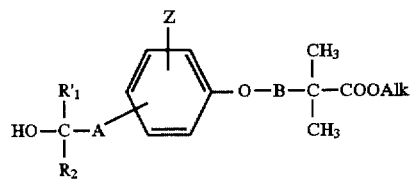  (IIIb)

wherein R'₁, R₂, A, Z, B and Alk are as defined above, to obtain a compound of formula Ib₁:

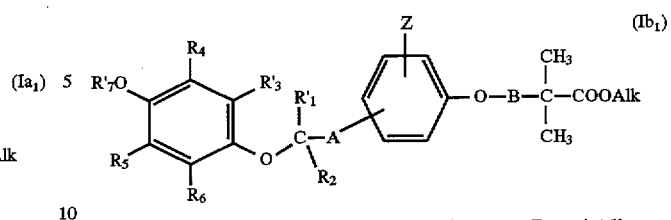  (Ib₁)

wherein R'₁, R₂, R'₃, R₄, R₅, R₆, R'₇, A, Z, B and Alk are as defined above, which compound of formula Ib₁ is, depending on the nature of R'₇, converted by sequential methods of saponification, hydrolysis or hydrogenolysis into a compound of formula Ib₂:

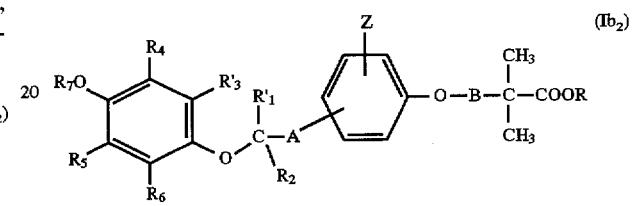  (Ib₂)

wherein R'₁, R₂, R'₃, R₄, R₅, R₆, R₇, A, Z, B and R are as defined above;

c) or a compound of formula IIc:

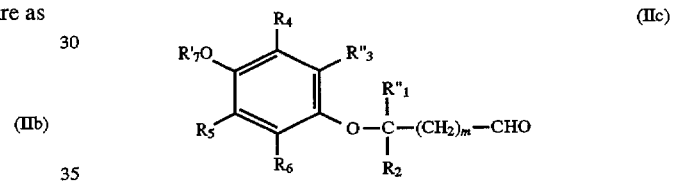  (IIc)

wherein:

R₂, R₄, R₅, R₆ and R'₇ are as defined above,

R"₁ and R"₃ together represent a (CH₂)ₙ bridge wherein n is as defined above, and m represents zero or an integer of from 1 to 5 inclusive;

is reacted with a compound of formula IIIc:

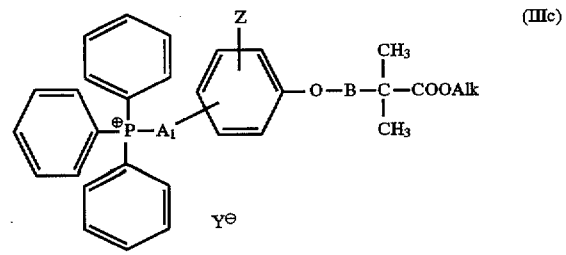  (IIIc)

wherein:

Alk, B, Z and Y are as defined above and

A₁ represents a hydrocarbon radical containing from 1 to 3 carbon atoms in straight or branched chain;

to obtain a compound of formula Ic₁:

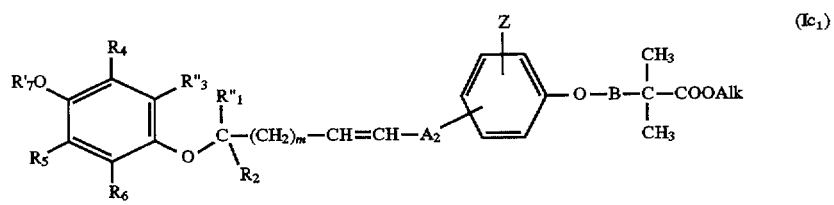  (Ic₁)

wherein:

R"$_1$, R$_2$, R"$_3$, R$_4$, R$_5$, R$_6$, R'$_7$, m, Z, B and Alk are as defined above and A$_2$ represents a single bond or a hydrocarbon radical containing 1 or 2 carbon atoms in straight or branched chain; which compound of formula Ic$_1$ is reduced to obtain the compound of formula Ic$_2$:

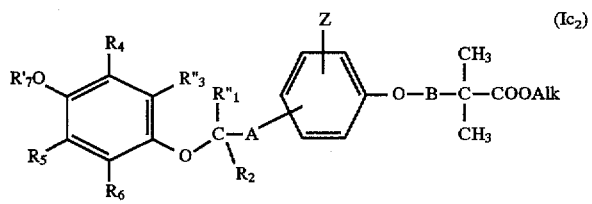

wherein R"$_1$, R$_2$, R"$_3$, R$_4$, R$_5$, R$_6$, R'$_7$, A, Z, B and Alk are as defined above;

which compound of formula Ic$_2$ is, depending on the nature of R'$_7$, converted by sequential methods of saponification, hydrolysis or hydrogenolysis into a compound of formula Ic$_3$:

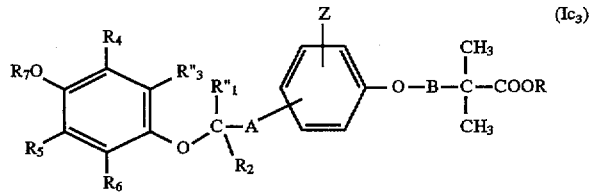

wherein R"$_1$, R$_2$, R"$_3$, R$_4$, R$_5$, R$_6$, R$_7$, A, Z, B and R are as defined above.

The totality of the compounds of formulae Ia$_1$, Ia$_2$, Ib$_1$, Ib$_2$, Ic$_1$, Ic$_2$ and Ic$_3$ form the totality of the compounds of formula I.

It is especially advantageous to react compounds of formulae IIa and IIIa in the presence of an acceptor for the hydracid formed during the course of the reaction in a solvent such as, for example, acetone, acetonitrile or dimethylformamide, at a temperature of from 50° to 120° C.

There may be used as acceptor, for example, an alkali metal carbonate in the presence of an alkali metal iodide, dimethylaminopyridine or triethylamine.

The reaction of compounds of formulae IIb and IIIb is carried out according to the method of O. Mitsunobu, Synthesis (1981), 1–28, using as reagents ethyl azodicarboxylate and triphenylphosphine and carrying out the reaction in an aprotic solvent, such as, for example, tetrahydrofuran or ether, at a temperature of from 20° to 25° C.

The reaction of compounds of formulae IIc and IIIc is advantageously carried out according to the method of Wittig G., Ann. (1953), 580, 44 and Brace et al., Chem. Rev. (1989), 863–927, using butyllithium as reagent and carrying out the reaction in tetrahydrofuran medium at a temperature of from 20° to 25° C.

One variant of that method, which gives higher yields, is carried out according to Buddrus, Chem. Ber. (1974), 107, 2050–61. In that case the reaction is carried out in the presence of excess 1,2-epoxybutane, which acts both as reagent and solvent, at the reflux temperature (63° C.).

The catalytic hydrogenation of the compound Ic$_1$ is carried out by means of palladium-on-carbon under a pressure of 5×10$^5$ Pa, in ethanol, at a temperature of from 20° to 25° C.

The starting materials of formulae IIa and IIb are commercial products that are already described in the literature.

The starting materials of formulae IIc are also described in the literature and are prepared according to N. Cohen et al., J. Am. Chem. Soc. 101, 6710–15 (1979) or according to Takeda, E.P. 345 593.

The starting materials of formula IIIb are obtained according to a process which comprises deprotecting in acid medium, for example in ethanolic HCl, a compound of formula IV:

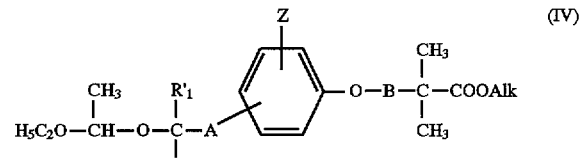

wherein R'$_1$, R$_2$, A, Z, B and Alk are as defined above.

That compound IV is itself obtained by reacting a compound of formula V:

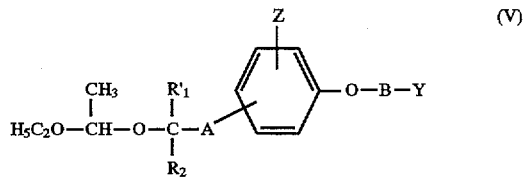

wherein R'$_1$, R$_2$, A, Z, B and Y are as defined above, with an alkyl isobutyrate, such as, for example, ethyl isobutyrate, in the presence of a strong base, such as, for example, lithium diisopropylamide, in an aprotic solvent, such as, for example, tetrahydrofuran.

That compound of formula V is obtained by reacting a compound of formula VI:

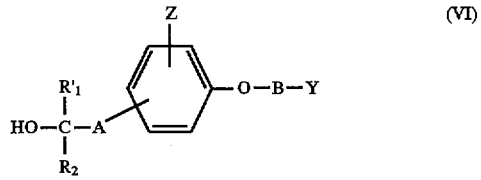

wherein R'$_1$, R$_2$, A, Z, B and Y are as defined above, with ethyl vinyl ether in an aprotic solvent, such as, for example, dichloromethane, in the presence of a hydracid or a strong acid, such as, for example, trichloroacetic acid.

The compound of formula VI is itself obtained by reacting a compound of formula VII:

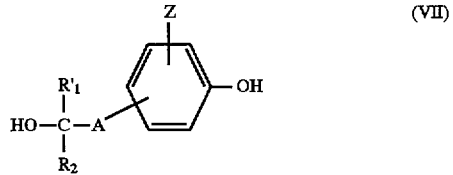

wherein R'$_1$, R$_2$, A and Z are as defined above with a ω-dichloro- or a ω-dibromo-alkane, in a polar aprotic solvent, such as, for example, methyl isobutyl ketone, in the presence of an alkali metal carbonate.

The starting materials of formula IIIa are obtained by reacting compounds of formula IIIb with triphenylphosphine in the presence of CCl$_4$ or of bromine in acetonitrile according to the method of J. Hooz et al., Can. J. Chem. 46, 86–7 (1968) or of J. Schaefer et al., Org. Synth. collect. vol V, 249.

The starting materials of formula IIIc are prepared in amorphous non-crystlline form according to the conventional method which comprises reacting a compound of formula IIIa as defined above with triphenylphosphine at reflux, in a polar aprotic solvent, such as, for example acetonitrile.

The compounds of formula I so obtained may be purified by flash chromatography on silica (35–70μ) using as eluant ethyl acetate or a $CH_2Cl_2/CH_3OH$ mixture, or by salt formation and crystallisation of the salts.

Some compounds of formula I yield salts with physiologically tolerable bases—which salts, as such, are included in the present invention.

The compounds of the present invention have valuable pharmacological and therapeutic activities, especially a protective activity against the oxidation of human LDLs (low density lipoproteins) and a hypolipaemic activity, which enable them to be used as medicaments especially in the treatment of:

hypercholesterolaemia, hypertriglyceridaemia, dyslipaemia and diabetes for the avoidance of complications, especially vascular complications, atherosclerosis with its different vascular locations: peripheral, coronary or cerebral, but also in pathologies in which membrane lipid peroxidation plays an initiating and/or aggravating role, such as ischaemic cardiopathies, the reperfusion of organs, including transplanted organs, traumatic or degenerative ischaemic pathologies of the central or peripheral nervous system, acute or chronic inflammatory disorders and auto-immune diseases.

The present invention relates also to pharmaceutical compositions comprising as active ingredient a compound of formula I or a physiologically tolerable salt thereof, mixed with or associated with an appropriate pharmaceutical excipient, such as, for example, glucose, lactose, starch, talc, ethylcellulose, magnesium stearate or cocoa butter.

Those compositions are generally presented in dosage form and may contain from 100 to 500 mg of active ingredient.

They may, for example, be in the form of tablets, dragées, gelatin capsules, suppositories, injectable or drinkable solutions and, depending on the case in question, may be administered by the oral, rectal or parenteral route at a dose of from 100 to 1500 mg taken in from 1 to 3 daily administrations.

The following Examples illustrate the present invention, the melting points being determined using a Kofler hot plate (K) or a capillary tube (cap).

EXAMPLE 1

2,2-Dimethyl-5-{4-[2-(3,5-di-tert-butyl-4-hydroxyphenylthio)ethyl]phenoxy}pentanoic acid, and its tert-butylamine salt.

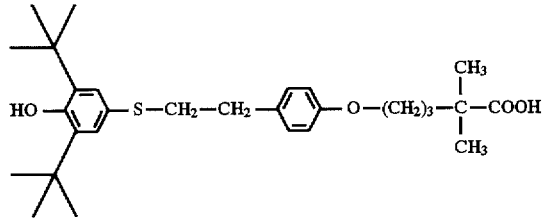

6.9 g (0.02 mol) of ethyl 2,2-dimethyl-5-[4-(2-bromoethyl)phenoxy]pentanoate, 5.3 g (0.022 mol) of 3,5-di-tert-butyl-4-hydroxyphenylthiol, 3 g of potassium carbonate, 0.3 g of potassium iodide and 200 ml of acetone are heated to reflux, and refluxing is maintained for 20 hours. The whole is filtered and concentrated to dryness, and the residue is taken up in dichloromethane, washed with water and dried over sodium sulphate.

After concentration to dryness, the residue is chromatographed on silica using a mixture of dichloromethane and cyclohexane (50-50) as eluant. 9.35 g of the expected ester are obtained in the form of a gum (yield: 91%). 5.9 g (0.0115 mol) of ethyl 2,2-dimethyl-5-{4-[2-(3,5-di-tert-butyl-4-hydroxyphenylthio)ethyl]phenoxy}pentanoate, 16.1 ml of N sodium hydroxide solution and 100 ml of ethanol are heated to reflux and refluxing is maintained for 24 hours. After cooling, the reaction mixture is acidified with N hydrochloric acid and then concentrated to dryness. The residue is taken up in ether, washed with water, dried over sodium sulphate and concentrated to dryness. The residue is chromatographed on 180 g of silica using a mixture of dichloromethane and acetone (95-5) as eluant. The expected acid is obtained in the form of a gum which is dissolved in ether and excess tert-butylamine is added. Crystallisation is observed. After filtration, suctioning off and drying at 40° C., under a pressure of 133 Pa, 4.6 g of the tert-butylamine salt of 2,2-dimethyl-5-{4-[2-(3,5-di-tert-butyl-4-hydroxyphenylthio)ethyl]phenoxy}pentanoic acid, m.p. (cap): 118°–121° C., are obtained (yield: 72%).

EXAMPLES 2–8

The compounds forming the subject of the following Examples were prepared by proceeding as described in Example 1:

2) 2,2-dimethyl-5-{4-[2-(3,5-di-tert-butyl-4-hydroxyphenylthio)ethyl]phenoxy}pentanoic acid and its tert-butylamine salt, m.p. (K): 110° C. (ether).

3) 2,2-dimethyl-5-{4-[3-(3,5-di-tert-butyl-4-hydroxyphenylthio)propyl]phenoxy}pentanoic acid and its tert-butylamine salt, m.p. (cap): 132°–138° C. (ether-pentane).

4) 2,2-dimethyl-5-{4-[3-(4-hydroxy-2,3,5-trimethylphenylthio)propyl]phenoxy}pentanoic acid, m.p. (cap): 68°–70° C. (dichloromethane).

5) 2,2-dimethyl-5-{4-[3-(3,5-di-tert-butyl-4-hydroxyphenylthio)propyloxy]phenoxy}pentanoic acid and its tert-butylamine salt, m.p. (cap): 135°–138° C. (ether).

6) 2,2-dimethyl-5-{4-[3-(4-hydroxy-2,3,5-trimethylphenylthio)propyloxy]phenoxy}pentanoic acid and its tert-butylamine salt, m.p. (cap): 122°–126° C. (ether).

7) 2,2-dimethyl-5-{3-[2-(4-hydroxy-2,3,5-trimethylphenylthio)ethyl]phenoxy}pentanoic acid, m.p. (cap): 72°–76° C. (dichloromethane).

8) 2,2-dimethyl-5-{3-[2-(3,5-di-tert-butyl-4-hydroxyphenylthio)ethyl]phenoxy}pentanoic acid, m.p. (cap): 102°–103° C. (dichloromethane-acetone).

EXAMPLE 9

2,2-dimethyl-5-{4-[2-(4-hydroxy-2,3,5-trimethylphenoxy)ethyl]phenoxy}pentanoic acid, and its tert-butylamine salt.

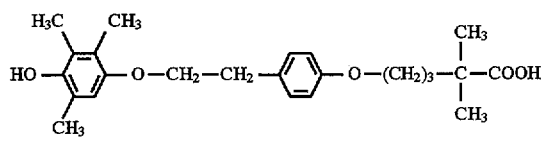

15.67 g of ethyl azodicarboxylate are poured dropwise into a mixture containing 11.6 g (0.06 mol) of 4-acetoxy-2,3,5-trimethylphenol melting (K) at 108° C., 23.6 g of triphenylphosphine, 500 ml of tetrahydrofuran and 19.2 g (0.065 mol) of ethyl 2,2-dimethyl-5-[4-(2-hydroxyethyl)phenoxy]pentanoate. The whole is stirred for one night at room temperature and is then concentrated to dryness. Cyclohexane is added, the whole is triturated and insoluble material is filtered off. The filtrate is concentrated to dryness and chromatographed on 1.16 kg of silica using dichloromethane as eluant. 10.9 g of the expected ester are obtained in the form of a thick oil (yield: 39%). 10.9 g of ethyl 2,2-dimethyl-5-{4-[2-(4-acetoxy-2,3,5-trimethylphenoxy)ethyl]phenoxy}pentanoate are heated at reflux for 3 hours with 500 ml of ethanol and 80 ml of N sodium hydroxide solution under a nitrogen atmosphere. After cooling, acidification is carried out with 100 ml of N hydrochloric acid and the solution is then concentrated to dryness. The residue is taken up in ether. The resulting solution is washed with water, dried over sodium sulphate and concentrated to dryness. The residue is chromatographed on 340 g of silica using a dichloromethane-acetone mixture (90-10) as eluant. 4.4 g of the desired acid are obtained in the form of a gum which is dissolved in 50 ml of ethyl ether. 1.3 ml of tert-butylamine are added to that solution. Crystallisation is observed and the resulting salt is filtered, suctioned off, washed with ether and then dried at 50° C. under a pressure of 133 Pa. 2.65 g of the tert-butylamine salt of 2,2-dimethyl-5-{4-[2-(4-hydroxy-2,3,5-trimethylphenoxy)ethyl]phenoxy}pentanoic acid, m.p. (K): 126° C., are obtained (yield: 24.5%).

EXAMPLES 10–16

The compounds forming the subject of the following Examples were prepared by proceeding as described in Example 9:

10) 2,2-dimethyl-5-{4-[3-(3,5-di-tert-butyl-4-hydroxyphenoxy)propyl]phenoxy}pentanoic acid, m.p. (cap): 118°–121° C. (dichloromethane).

11) 2,2-dimethyl-5-{4-[3-(4-hydroxy-2,3,5-trimethylphenoxy)propyloxy]phenoxy}pentanoic acid, m.p.: 80°–85° C. (dichloromethane-acetone).

12) 2,2-dimethyl-5-{4-[3-(3,5-di-tert-butyl-4-hydroxyphenoxy)propyloxy]phenoxy}pentanoic acid and its tert-butylamine salt, m.p. (cap): 146°–149° C. (ether).

13) 2,2-dimethyl-5-{3-[2-(3,5-di-tert-butyl-4-hydroxyphenoxy)ethyl]phenoxy}pentanoic acid and its tert-butylamine salt, m.p. (cap): 121°–125° C. (ether).

14) 2,2-dimethyl-5-{3-[2-(4-hydroxy-2,3,5-trimethylphenoxy)ethyl]phenoxy}pentanoic acid and its tert-butylamine salt, m.p. (cap): 118°–120° C. (ether-pentane).

15) 2,2-dimethyl-5-{4-[3-(4-hydroxy-2,3,5-trimethylphenoxy)propyl]phenoxy}pentanoic acid and its tert-butylamine salt, m.p. (cap): 126°–130° C. (ether).

16) 2,2-dimethyl-5-{4-[2-(4-hydroxy-3,5-di-tert-butylphenoxy)ethyl]phenoxy}pentanoic acid, m.p. (K): 114° C. (ethanol).

EXAMPLE 17

R,S-2,2-dimethyl-5-{4-[4-(6-hydroxy-2,5,7,8-tetramethyl-3,4-dihydrobenzopyran-2-yl)but-3-enyloxy]phenoxy}pentanoic acid

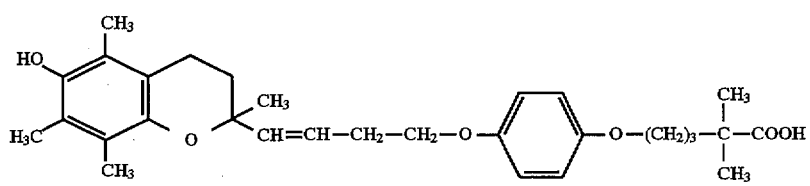

A mixture containing 27.3 g (0.042 mol) of 3-[4-(4,4-dimethyl-4-ethoxycarbonylbutoxy)phenoxy]propyltriphenylphosphonium bromide, 12.2 g (0.042 mol) of 6-ethoxymethoxy-2-formyl-2,5,7,8-tetramethyl-3,4-dihydrobenzopyran and 1.2 l of 1,2-epoxybutane are heated at reflux for 72 hours. The whole is concentrated to dryness and the residue is chromatographed on 1.1 kg of silica using a mixture of dichloromethane and cyclohexane (50-50) as eluant. 16.6 g of ethyl R,S-2,2-dimethyl-5-{4-[4-(6-ethoxymethoxy-2,5,7,8-tetramethyl-3,4-dihydrobenzopyran-2-yl)but-3-enyloxy]phenoxy}pentanoate are obtained in the form of a gummy mixture of E and Z (yield: 67%).

The 6-ethoxymethoxy-2-formyl-2,5,7,8-tetramethylchromane used as starting material was prepared by reduction with diisobutylaluminum hydride of the corresponding methyl ester (oil nD20° C.=1.5207) itself prepared from the methyl ester of trolox and chloromethyl ethyl ether in dimethylformamide in the presence of sodium hydride.

The 3-[4-(4,4-dimethyl-4-ethoxycarbonylbutoxy)phenoxy]propyltriphenylphosphonium bromide used as starting material was prepared by reacting triphenylphosphine in acetonitrile, at reflux, with ethyl 2,2-dimethyl-5-[4-(3-bromopropyloxy)phenoxy]pentanoate, itself obtained from ethyl 5-[4-(3-hydroxypropyloxy)phenoxy]pentanoate and bromine in acetonitrile in the presence of triphenylphosphine.

The ethyl R,S-2,2-dimethyl-5-{4-[4-(6-ethoxymethoxy-2,5,7,8-tetramethyl-3,4-dihydrobenzopyran-2-yl)but-3-enyloxy]phenoxy}pentanoate obtained above is saponified in a mixture of ethanol and N sodium hydroxide solution at reflux, and deprotected in 4N hydrochloric dioxane. 4.8 g of the expected acid, m.p. (cap): 70°–75° C. (petroleum ether), are obtained (yield: 35%).

EXAMPLE 18

R,S -2,2-dimethyl-5-{4-[4-(6-hydroxy-2,5,7,8-tetramethyl-3,4-dihydrobenzopyran-2-yl)butyloxy]phenoxy}pentanoic acid.

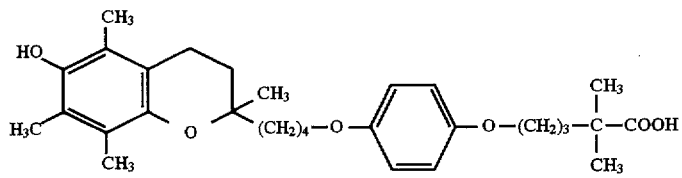

6.8 g (0.0137 mol) of R,S-2,2-dimethyl-5-{4-[4-(6-hydroxy-2,5,7,8-tetramethyl-3,4-dihydrobenzopyran-2-yl)but-3-enyloxy]phenoxy}pentanoic acid (prepared according to Example 17) dissolved in 200 ml of ethanol are hydrogenated in the presence of 1 g of 5% palladium-on-carbon in a Parr apparatus at room temperature under a pressure of $5\times10^5$ Pa. The whole is filtered and concentrated to dryness and then chromatographed on 340 g of silica using a toluene-tetrahydrofuran mixture (90-10) as eluant. 2.65 g of the expected acid, m.p. (cap): 90°–94° C., are obtained (yield: 39%).

EXAMPLES 19–20

The compounds forming the subject of the following Examples were prepared by proceeding as described in Example 18:

19) R,S-2,2-dimethyl-5-{3-[3-(6-hydroxy-2,5,7,8-tetramethyl-3,4-dihydrobenzopyran-2-yl)-propyl]phenoxy}pentanoic acid and its sodium salt in the form of a lyophilisate.

The ethyl R,S-2,2-dimethyl-5-{3-[3-(6-ethoxy-2,5,7,8-tetramethyl-3,4-dihydrobenzopyran-2-yl)propyl]phenoxy}pentanoate intermediate was prepared according to the method described in Example 17.

20) 2,2-dimethyl-5-{3-[3-(4-hydroxy-3,5-di-tert-butylphenyl)propyl]phenoxy}pentanoic acid and its tert-butylamine salt, m.p. (cap): 97°–100° C. (pentane).

The ethyl 2,2-dimethyl-5-{3-[3-(4-ethoxymethoxy-3,5-di-tert-butylphenyl)propyl]phenoxy}pentanoate intermediate was prepared according to the method described in Example 17.

EXAMPLE 21

Pharmacological study

1. PROTECTIVE ACTIVITY AGAINST OXIDATION OF LDLs

The anti-oxidant effect of the compounds of the present invention was demonstrated in vitro on the peroxidation of human low density lipoproteins (LDLs) induced by copper sulphate. The dose-effect relationship of those compounds was compared with that of probucol and a soluble analogue of vitamin E, trolox.

A. METHODS

The anti-oxidant activity of the compounds was measured according to the method of Wallin et al. (Analytical Biochemistry, 1993, 208, 10–15).

a) LDL oxidation reaction

Human LDLs are incubated for 3 hours at 37° C. in the presence of an oxidising agent, copper sulphate at a concentration of 5 µM, and of the compound to be tested at concentrations ranging from $10^{-8}$M to $2.5\times10^{-6}$M. A non-oxidised control (LDLs only) and an oxidised control (LDLs plus copper sulphate) are also included in each of the series of tests.

b) Determination of TBARS

The products of the LDL oxidation reaction are quantified by the colorimetric determination of "thiobarbituric acid reactive substances" (TBARS).

B. RESULTS

The protective activity of the tested compounds is expressed by the $IC_{50}$ value, which corresponds to the concentration of product required to inhibit by 50% the oxidation of LDLs observed in the absence of product. The $IC_{50}$ value was calculated from the dose-response curve.

The $IC_{50}$s obtained for each of the tested compounds are shown in Table A. All of the compounds tested are more active than the reference compounds, and the compounds of Examples 1 to 19 have an $IC_{50}$ ranging from $1.7\times10^{-7}$M to $6.8\times10^{-8}$M. Those results indicate a protecting activity against the oxidation of LDLs that is 10 to 70 times greater than that exerted by the reference compounds probucol and trolox.

TABLE A

| Protection against the oxidation of LDLs | |
|---|---|
| Compounds | $IC_{50}$ (M) |
| Example 1 | $4.2 \times 10^{-7}$ |
| Example 2 | $2.1 \times 10^{-7}$ |
| Example 3 | $5.3 \times 10^{-7}$ |
| Example 4 | $4.6 \times 10^{-7}$ |
| Example 5 | $5.5 \times 10^{-7}$ |
| Example 6 | $1.7 \times 10^{-7}$ |
| Example 7 | $6.8 \times 10^{-8}$ |
| Example 8 | $3.8 \times 10^{-7}$ |
| Example 9 | $2.0 \times 10^{-7}$ |
| Example 10 | $2.4 \times 10^{-7}$ |
| Example 11 | $1.9 \times 10^{-7}$ |
| Example 12 | $6.4 \times 10^{-7}$ |
| Example 13 | $3 \times 10^{-7}$ |
| Example 14 | $8.8 \times 10^{-8}$ |
| Example 15 | $9.7 \times 10^{-8}$ |
| Example 16 | $7.7 \times 10^{-7}$ |
| Example 17 | $9.6 \times 10^{-7}$ |
| Example 18 | $7.2 \times 10^{-7}$ |
| Example 19 | $6.8 \times 10^{-7}$ |
| Example 20 | $1.1 \times 10^{-6}$ |
| Probucol | $5.8 \times 10^{-6}$ |
| Trolox | $1.6 \times 10^{-6}$ |

2. HYPOLIPAEMIC ACTIVITY

The hypolipaemic activity of certain representative compounds of the invention was evaluated in vivo in a diet-induced model of combined hyperlipaemia in the hamster.

A. METHODS

Golden Syrian hamsters are given a diet rich in lipids (standard diet+0.5% cholesterol+10% cocoa oil) for 3 weeks before the beginning of treatment. That diet induces hypercholesterolaemia and hypertriglyceridaemia.

The products are prepared in tragacanth gum and are administered per os by forced gastric feeding for 1 week at a dose of 200 mg/kg/day. Each product is tested on a group of 6 animals. A placebo group (control) and a group of animals treated with a reference product (bezafibrate at a dose of 200 mg/kg/day) are included in each experiment.

At the end of the treatment, the animals are anaesthetised with ether. Blood is removed by abdominal puncture and the triglycerides and total cholesterol in the serums are determined. Five independent experiments were carried out in accordance with that protocol in order to evaluate the hypolipaemic effect of thirteen compounds of this invention.

B. RESULTS

The results are shown in Table B. The effect of the treatment is expressed as a percentage variation by comparison with the control group, calculated from the means of the absolute values of triglycerides and of total cholesterol. A negative value thus reflects a hypolipaemic effect of the treatment indicated. The values shown for bezafibrate represent the mean values (±sem) of five experiments.

TABLE B

Effect of the products on the plasma lipids

| Compounds | Triglycerides (% variation/control) | Total cholesterol (% variation/control) |
|---|---|---|
| Example 2 | −82 | −52 |
| Example 3 | −87 | −77 |
| Example 4 | −77 | −48 |
| Example 6 | −59 | −39 |
| Example 7 | −83 | −47 |
| Example 8 | −59 | −59 |
| Example 11 | −60 | −55 |
| Example 12 | −84 | −63 |
| Example 13 | −84 | −68 |
| Example 15 | −93 | −77 |
| Example 16 | −54 | −66 |
| Example 18 | −79 | −61 |
| Example 20 | −71 | −58 |
| Bezafibrate | −46 ± 19 | −48 ± 4 |

All of the compounds tested reduce the plasma triglycerides. Examples 2, 3, 7, 12, 13 and 15 are statistically at least as effective as bezafibrate. Those 6 compounds also exert a hypocholesterolaemic effect at least as great as bezafibrate.

3. CONCLUSION

The results shown above demonstrate that the compounds of the present invention have a dual activity:

a protective effect against the oxidation of LDLs, with an efficacy 10 to 70 times greater than that of the reference compounds probucol and trolox.

a hypocholesterolaemic and hypotriglyceridaemic effect. Of the products tested, six have an activity at least as great as that of the reference fibrate, bezafibrate.

No reference product combines those two effects.

We claim:

1. A compound selected from the group consisting of:

substituted 2,2-dimethyl-ω-phenoxyalkanoic acids and esters of formula I:

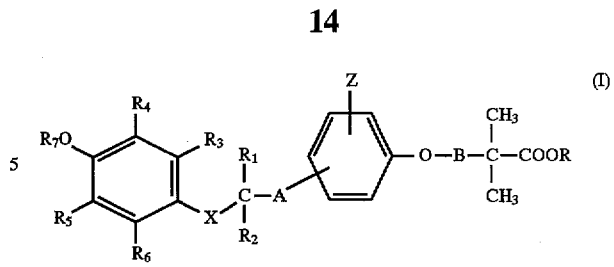

wherein:

X represents oxygen, sulfur, or a single bond;

A represents a single bond, or a $(C_1-C_9)$ hydrocarbon group in straight or branched chain and optionally containing a double bond or oxygen;

B represents a $(C_1-C_9)$ hydrocarbon group in straight or branched chain;

R represents hydrogen, or $(C_1-C_6)$ alkyl in straight or branched chain which is optionally substituted by one or two hydroxy;

$R_1$ and $R_3$:
each simultaneously represents hydrogen, or
together they form a $(CH_2)_n$ bridge wherein n has a value of 1 or 2 except in the case where X represents a single bond, or
$R_1$ represents
methyl, or
a single bond forming a double bond with the group A when that group is a hydrocarbon group and, in each of those cases $R_3$ simultaneously represents hydrogen;

$R_2$ and $R_6$, which are identical or different, each represents hydrogen or methyl;

$R_4$ and $R_5$, which are identical or different, each represents $(C_1-C_6)$ alkyl in straight or branched chain;

$R_7$ represents hydrogen or a labile protecting group; and

Z represents hydrogen, halogen, or $(C_1-C_5)$ alkyl or $(C_1-C_5)$ alkoxy each in straight or branched chain;

*enantiomers and diastereoisomers thereof, and

*physiologically-tolerable salts thereof with pharmaceutically-acceptable bases.

2. A compound of claim 1 which is selected from the group consisting of 2,2-dimethyl-5-{4-[2-(3,5-di-tert-butyl-4-hydroxyphenylthio)ethyl]phenoxy}pentanoic acid and its tert-butylamine salt.

3. A compound of claim 1 which is selected from the group consisting of 2,2-dimethyl-5-{4-[3-(3,5-di-tert-butyl-4-hydroxyphenylthio)propyl]phenoxy}pentanoic acid and its tert-butylamine salt.

4. A compound of claim 1 which is 2,2-dimethyl-5-{3-[2-(4-hydroxy-2,3,5-trimethylphenylthio)ethyl]phenoxy}pentanoic acid.

5. A compound of claim 1 which is selected from the group consisting of 2,2-dimethyl-5-{4-[3-(3,5-di-tert-butyl-4-hydroxyphenoxy)propyloxy]phenoxy}pentanoic acid and its tert-butylamine salt.

6. A compound of claim 1 which is selected from the group consisting of 2,2-dimethyl-5-{3-[2-(3,5-di-tert-butyl-4-hydroxyphenoxy)ethyl]phenoxy}pentanoic acid and its tert-butylamine salt.

7. A compound of claim 1 which is selected from the group consisting of 2,2-dimethyl-5-{4-[3-(4-hydroxy-2,3,5-trimethylphenoxy)propyl]phenoxy}pentanoic acid and its tert-butylamine salt.

8. A method for treating a living animal body afflicted with hypercholesterolaemia, hypertriglyceridaemia, dyslipaemia, diabetes, atherosclerosis, or a pathology in which membrane lipid peroxidation plays an initiating and/or aggravating role, which comprises the step of administering to the said living animal body an amount of a compound of claim 1 which is effective for alleviation of said condition.

9. A pharmaceutical composition having a protective activity against the oxidation of human LDLs and a hypolipaemic activity, comprising as active ingredient an effective amount of a compound according to claim 1 together with one or more pharmaceutically-acceptable excipients.

* * * * *

UNITED STATES PATENT AND TRADEMARK OFFICE
CERTIFICATE OF CORRECTION

PATENT NO. : 5,734,077
DATED : March 31, 1998
INVENTOR(S) : G. Regnier, C. Guillonneau, J.P. Vilaine, F. Mahlberg, C. Breaugnot It is certified that error appears in the above-indentified patent and that said Letters Patent is hereby corrected as shown below:

Title Page, [73] Assignee: "Adir ET Compagnie" should read -- ADIR ET COMPAGNIE --.

Column 6, line 66: "non-crystlline" should read -- non-crystalline --.

Column 10, line 43: "nD20°" should read -- $n_D^{20°}$ --.

Signed and Sealed this

Twenty-third Day of June, 1998

Attest:

BRUCE LEHMAN

*Attesting Officer*   *Commissioner of Patents and Trademarks*